(12) United States Patent
Fischer et al.

(10) Patent No.: US 7,974,378 B2
(45) Date of Patent: Jul. 5, 2011

(54) METHOD FOR POSITIONING THE BREAST FOR A BIOPSY IN A MAMMOGRAPHY DEVICE, AND MAMMOGRAPHY DEVICE TO IMPLEMENT THE METHOD

(75) Inventors: Daniel Fischer, Erlangen (DE); Carina Hofmann, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 75 days.

(21) Appl. No.: 12/529,209

(22) PCT Filed: Sep. 12, 2008

(86) PCT No.: PCT/EP2008/062148
§ 371 (c)(1),
(2), (4) Date: Aug. 31, 2009

(87) PCT Pub. No.: WO2009/080378
PCT Pub. Date: Jul. 2, 2009

(65) Prior Publication Data
US 2010/0054402 A1    Mar. 4, 2010

(30) Foreign Application Priority Data

Dec. 20, 2007    (DE) .......................... 10 2007 061 592

(51) Int. Cl.
*A61B 6/04*    (2006.01)

(52) U.S. Cl. .......................................... 378/37; 378/205
(58) Field of Classification Search .................... 378/37, 378/63, 205, 206
See application file for complete search history.

(56) References Cited

U.S. PATENT DOCUMENTS

| | | |
|---|---|---|
| 5,572,565 A | 11/1996 | Abdel-Mottaleb |
| 6,731,966 B1 | 5/2004 | Spigelman et al. |
| 2004/0101096 A1 | 5/2004 | Tsujii |
| 2006/0093084 A1 | 5/2006 | Gutman |
| 2007/0139799 A1 | 6/2007 | Ramsauer |
| 2007/0183565 A1 | 8/2007 | Brandstatter et al. |
| 2007/0225600 A1 | 9/2007 | Weibrecht et al. |

FOREIGN PATENT DOCUMENTS

| | | |
|---|---|---|
| DE | 10 2005 031 118 A1 | 1/2007 |
| WO | WO 2007/023050 A1 | 3/2007 |

*Primary Examiner* — Jurie Yun
(74) *Attorney, Agent, or Firm* — Schiff Hardin LLP

(57) ABSTRACT

In a method and a mammography device, a virtual mask is created from an x-ray image of the breast for positioning the breast for a biopsy. The mask reproduces the image region covered by the breast tissue. A region targeted for the biopsy, and located within the breast tissue, is marked in the mask. The breast is then positioned for the biopsy in the mammography device between a support plate and a compression plate, the compression plate being provided with a recess for introducing the biopsy instrument therethrough. The mask and the compression plate are superimposed to cause the marked region to be located within this recess. The breast is then moved until the position and the contour thereof substantially coincide with the position and contour of the mask.

15 Claims, 2 Drawing Sheets

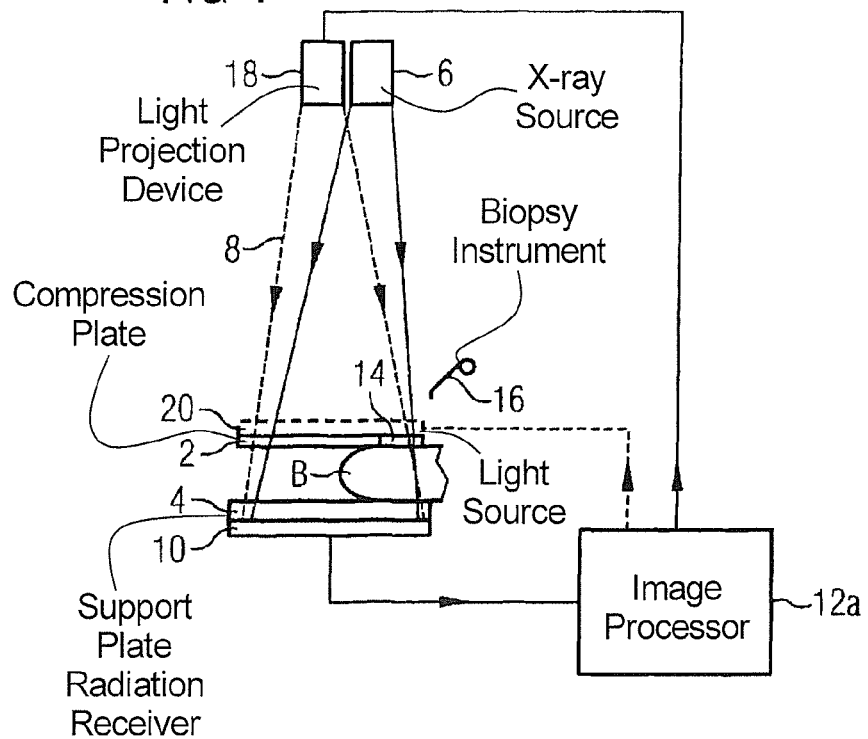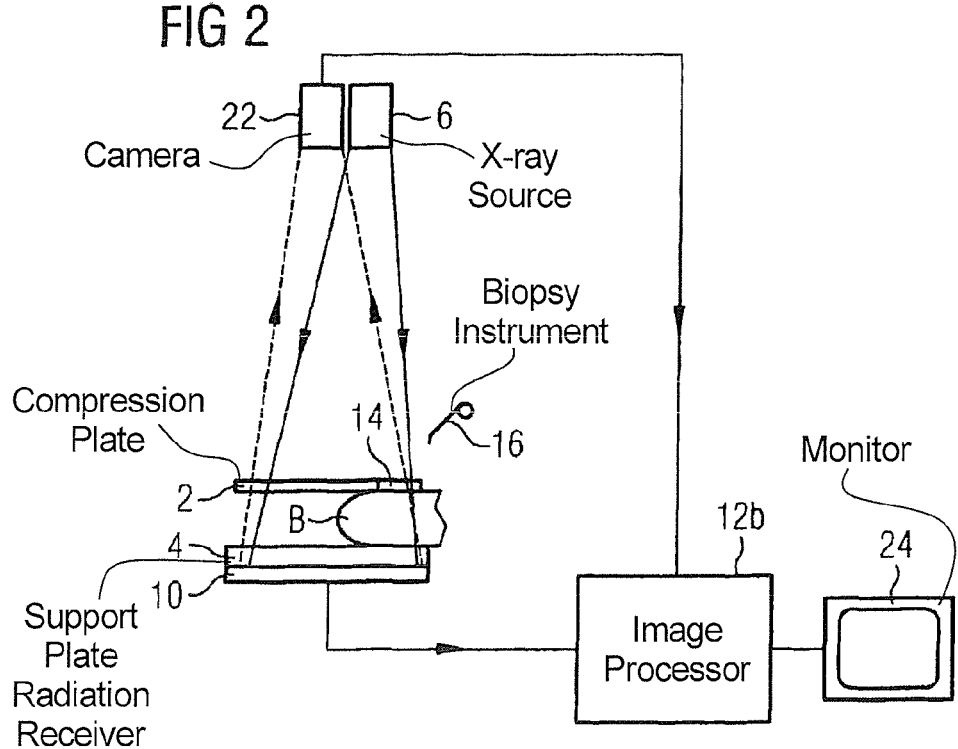

METHOD FOR POSITIONING THE BREAST FOR A BIOPSY IN A MAMMOGRAPHY DEVICE, AND MAMMOGRAPHY DEVICE TO IMPLEMENT THE METHOD

BACKGROUND OF THE INVENTION

1. Field of the Invention

The present invention concerns a method for positioning the breast for a biopsy in a mammography device. Moreover, the invention concerns a mammography device to implement this method.

2. Description of the Prior Art

When a pathological tissue variation or lesion is established in an x-ray image of the breast within the framework of a mammogram examination, for a definite diagnosis it is required in many cases to extract a tissue sample and to histologically examine this. For this purpose, in the stereotactic biopsy the breast is compressed and fixed between a compression plate and a bearing plate in a mammography device. The compression plate contains a rectangular opening via which the biopsy instrument can be inserted into the breast. In order to ensure that the tissue sample is extracted at the correct point, x-ray exposures are created from different directions during the procedure and the lesion is marked in the x-ray exposures. The precise penetration position and position depth of the biopsy instrument can be determined in this way. Before these x-ray acquisitions, the breast must now already be positioned so that the projection of the lesion is located within the projection of the rectangular opening. For correct positioning of the breast, it is therefore necessary to acquire one or more x-ray images from different directions before the acquisition of the x-ray images, which x-ray images serve exclusively to correctly position the breast between compression plate and bearing plate. However, every such x-ray acquisition entails an additional radiation exposure for the patient.

SUMMARY OF THE INVENTION

An object of the invention is to provide a method for positioning the breast for a biopsy in a mammography apparatus with which the number of the x-ray images required for correct positioning is reduced. Moreover, the invention is based on the object to specify a mammography apparatus to implement the method.

The object according to the invention is achieved by a method for positioning the breast for a biopsy in a mammography device that includes:

a) generating a virtual mask that reproduces the image region covered by the breast tissue and in which a region situated within the breast tissue and provided for the biopsy is marked from at least one x-ray image of the breast, b) for the biopsy in the mammography device, the breast is positioned between a bearing plate and a compression plate provided with an opening for the insertion of a biopsy instrument, c) the mask and the compression plate are superimposed such that the marked region is arranged within the opening, d) the breast is shifted until its position and contour coincide approximately with the position and contour of the mask.

The number of x-ray exposures required for correct positioning of the breast for the biopsy is distinctly reduced via this measure, wherein in the most advantageous case the necessity for the acquisition of an x-ray image is completely done away with since a stored x-ray image that has been acquired within the scope of a previous examination can be resorted to for the generation of the mask.

If a visible image (in particular a projection image projected onto the compression plate) is generated from the mask in the region of the compression plate such that the marked region in the projection image of the mask is arranged within the opening, and the breast is displaced until its position and contour at least approximately coincide with the position and contour of the image or projection image of the mask, a particularly simple and intuitive positioning of the breast is possible via direct comparison of the image or of the projection image with the breast situated below the image or projection image.

An additional simplification is achieved when a displacement vector that indicates in which direction and how far the breast must be displaced is shown in the projection image. This displacement vector can be calculated from the location of the marked region in the x-ray image and the location of the opening.

In an alternative embodiment of the method, a camera image of the breast and a portion of the compression plate having at least the opening is acquired, and the mask is superimposed on the camera image displayed on a monitor such that the marked region is arranged within the opening. The breast is then displaced until its position and contour in the camera image at least approximately coincide with the position and contour of the mask superimposed on the camera image. The camera image is advantageously acquired from a direction that corresponds at least approximately with the direction in which x-rays generated by an x-ray source or x-ray tube of the mammography device propagate.

The correct positioning is facilitated when a displacement vector that indicates in which direction and how far the breast must be displaced is shown in the camera image.

The displacement of the virtual mask in such a manner that the marked region is situated within the opening of the compression plate advantageously ensues automatically, like the generation of the virtual mask and the marked region.

The above object is also achieved in accordance with the present invention by a mammography device that is constructed and operated to implement the method described above, as well as all embodiments thereof.

The above object also is achieved in accordance with the present invention by a computer-readable medium that is loadable into a control unit of a mammography device, the computer-readable medium being encoded with programming instructions that cause the mammography device to be operated in accordance with the inventive method described above, as well as all embodiments thereof.

BRIEF DESCRIPTION OF THE DRAWINGS

FIG. 1 schematically illustrates a first embodiment of a mammography device constructed and operated in accordance with the present invention.

FIG. 2 schematically illustrates a second embodiment of a mammography device constructed and operated in accordance with the present invention.

DESCRIPTION OF THE PREFERRED EMBODIMENTS

Figure 3:
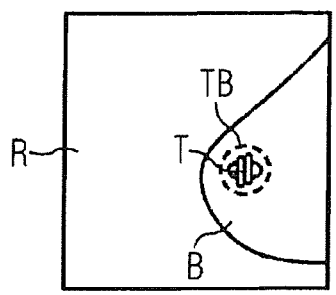
FIG. 3 schematically illustrates an x-ray image of a breast with a lesion therein.
Figure 4:
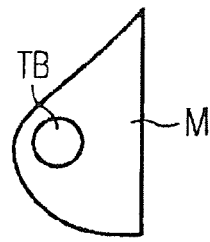
FIG. 4 schematically illustrates a virtual mask generated from the x-ray image in accordance with the present invention.

According to FIG. 1, a breast B is compressed and fixed between a compression plate 2 and a support plate 4 in a mammography device according to the invention. To generate an x-ray image of the breast B, x-rays 8 are generated by an x-ray source 6 and received (detected) by an x-ray receiver 10 arranged after the bearing plate 4. The image data acquired by the x-ray receiver 10 are processed in an image processor 12a.

The compression plate 2 has a rectangular opening 14 through which a biopsy instrument 16 can be inserted into the breast B. An x-ray image of the breast B that has been generated and assessed either shortly beforehand with the same mammography device or at a point in time further in the past with a different mammography device is located in the memory of the image processor 12a. From this x-ray image a virtual mask is now generated in the image processor 12a that renders the image region covered by the breast tissue in the x-ray image, i.e. whose edge coincides with the contour of the breast and in which a region situated within the breast tissue and provided for biopsy is marked. This can ensue automatically by segmenting methods of digital image processing.

With the use of a rendering device in the region of the compression plate 2, a visible image of the virtual mask determined in the image processor 12a is now generated. In the exemplary embodiment, the mask is projected onto the compression plate with a light projection device 18 so as to be visible to an observer (i.e. is visually imaged on the compression plate 2 so as to be recognizable to the observer) such that the marked region is arranged within the opening 14. The mask is recognizable on the compression plate 2 or the bearing plate 4 or, respectively, the breast B via contour lines that represent the outer contour of the breast and the marked region.

Using this projection image visible for the observer, the breast B can now be displaced so that its outer contour visible to the observer at least approximately coincides with the edge of the projection image of the mask. The breast is then correctly positioned between the compression plate 2 and support plate 4 since it is then ensured that the lesion located in the breast B is arranged in the region of the opening 14. The necessity for the acquisition of additional x-ray images that would exclusively serve the purpose of correctly positioning the breast is thus done away with.

The visual representation of the mask on the compression plate 2 or the bearing plate 4 can ensue via an LCD projector or via lines projected by a laser. In order to facilitate the recognition capability, the compression plate 2 can moreover be coated with a fluorescing material.

Instead of such a projection, it is alternatively also possible to arrange a light source 20 (for example an organic display) on the compression plate 2 that displays the mask and the marked region, as is illustrated with dashed lines in the Figure. In the event that this is necessary, this light source 20 can be removed from the beam path of the x-ray beam 8 in the following stereotactic biopsy.

To facilitate the correct positioning, a displacement vector can moreover be shown in the image or projection image, which displacement vector indicates in which direction and how far (i.e. which distance) the breast B must be displaced.

In the alternative embodiment according to FIG. 2, in addition to the x-ray source 6 a camera 22 is arranged that acquires a camera image of the breast B and a portion of the compression plate 2 having at least the opening 14. The camera image is shown on a monitor 24 with the aid of an image processing and image display device 12b. In the image processing and image display device 12b, a virtual mask is generated (as in the image processor 12a) from the x-ray image of the breast B that was generated in a previous examination, and said virtual mask is superimposed on the camera image such that the marked region is arranged within the opening 14. The breast B is then correctly positioned between compression plate 2 and bearing plate 4 when its camera image approximately coincides with the image of the mask reproduced on the monitor 24.

In FIGS. 1 and 2 both the projection device 18 and the camera 22 are arranged such that the compression plate 2 is located directly in the projection region of the projection device 18 or in the field of view of the camera 22. As an alternative to this, both the projection and the camera acquisition can ensue via deflection mirrors so that projection device 18 and the camera 22 do not need to be arranged directly next to the x-ray source 6.

A procedure according to the invention is subsequently explained using FIG. 3 through 7. According to FIG. 3, an x-ray image R of the breast B is generated (normally in the course of a prior examination) under conditions that correspond to the image acquisition conditions in the stereotactic biopsy. In this x-ray image R, a lesion T is detectable. With methods of digital image processing, via segmentation a virtual mask M (shown in FIG. 4) is created that renders the image region covered by the breast tissue and in which a region TB situated within the breast tissue is marked, within which region TB the lesion T is located.

Figure 5:
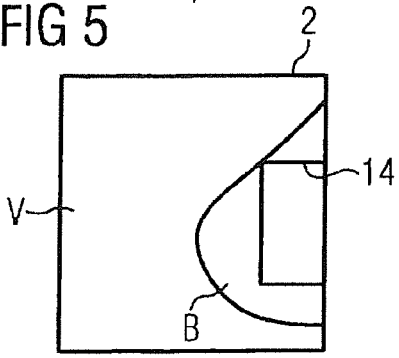
FIG. 5 schematically illustrates a camera image of the breast located beneath a compression plate that is provided with an opening, in accordance with the present invention.

In a following step, according to FIG. 5 the breast B is positioned between the compression plate 2 and the bearing plate 4 in the mammography device provided for the biopsy and is either directly visible to the observer or is shown indirectly on a monitor as a camera image V (acquired by a camera) with a likewise recognizable opening 14.

Figure 6:
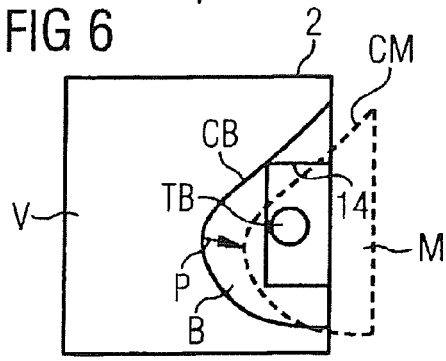
FIG. 6 shows the camera image of the breast from FIG. 5, with the virtual mask of FIG. 4 superimposed on this camera image.
Figure 7:
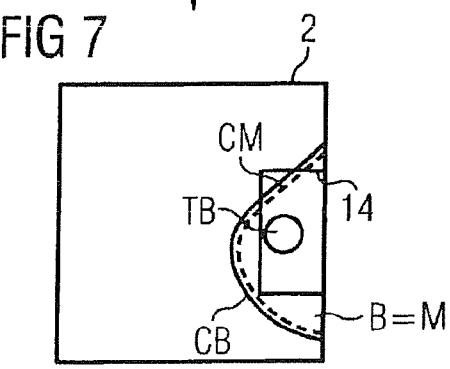
FIG. 7 schematically illustrates the camera image of the breast with the virtual mask superimposed thereon, after correct positioning of the breast.

According to FIG. 6, the mask M is now superimposed on the camera image V or indirectly on the compression plate 2 such that the marked region TB is arranged within the opening 14. The breast B is now displaced below the compression plate 2 into a position (shown in FIG. 7) in which its outer contour characterized by approximately coincides with the outer contour CM of the mask M. The marked region TB (and therefore the lesion located inside the breast) is then correctly positioned in the region of the opening 14.

Moreover, a displacement vector P that indicates in which direction the breast B must be displaced beneath the compression plate 2 is shown in FIG. 6. For example, the mamillae can serve as orientation markers to which the start point and end point of the displacement vector P can be attached.

Although modifications and changes may be suggested by those skilled in the art, it is the intention of the inventors to embody within the patent warranted heron all changes and modifications as reasonably and properly come within the scope of their contribution to the art.

We claim as our invention:
1. A method for positioning a breast for a biopsy in a mammography device, comprising the steps of:
  from at least one x-ray image of a breast, generating a virtual mask that reproduces an image region covered by breast tissue of the breast, and said virtual mask including a marked target region for a biopsy;
  positioning the breast between a support plate and a compression plate in a mammography device, said compression plate having an opening therein allowing insertion of a biopsy instrument through the compression plate into the breast;

superimposing the mask and the compression plate to cause said marked target region to be located within said opening; and while compressing the breast between the support plate and the compression plate, displacing the breast until a position and contour of the breast substantially coincide with a position and contour of the mask.

2. A method as claimed in claim 1 comprising automatically generating said virtual mask and marking said target region therein.

3. A method as claimed in claim 1 comprising automatically superimposing said mask and said compression plate.

4. A method as claimed in claim 1 comprising generating a visible image of said virtual mask on said compression plate, and displacing said breast until the position and contour of the breast substantially coincide with a position and contour of said image of said mask.

5. A method as claimed in claim 4 comprising generating said image of said mask on said compression plate as a projection image projected onto said compression plate.

6. A method as claimed in claim 4 comprising generating, in said image, a displacement vector that indicates a direction and extent for displacement of the breast that are necessary to cause the position and contour of the breast to substantially coincide with the position and contour of the image of the virtual mask.

7. A method as claimed in claim 1 comprising, with a camera, generating a camera image of the breast in the mammography device and a portion of the compression plate containing said opening, superimposing said virtual mask on said camera image with said marked target region in said opening in said camera image, and displacing the breast until a position and contour of the breast in the camera image substantially coincides with a position and contour of the mask superimposed on said camera image.

8. A method as claimed in claim 7 comprising, in said camera image, generating a displacement vector that indicates a direction and extent that are necessary to cause the position and contour of the breast in the camera image to substantially coincide with the position and contour of the virtual mask superimposed on the camera image.

9. A mammography device, comprising:
an x-ray imaging system that generates an x-ray image of a breast;
an image processor that, from said x-ray image of the breast, generates a virtual mask that reproduces an image region covered by breast tissue of the breast, and that marks a target region for a biopsy in said virtual mask;
a support plate and a compression plate adapted to receive and compress the breast therebetween, said compression plate having an opening therein allowing insertion of a biopsy instrument through the compression plate into the breast; and
a superimposing device configured to superimpose the mask and the compression plate to cause said marked target region to be located within said opening, and, while compressing the breast between the support plate and the compression plate, that allows the breast to be displaced until a position and contour of the breast substantially coincide with a position and contour of the mask.

10. A mammography device as claimed in claim 9 wherein said superimposing device comprises a display device at which a visible image of said mask on said compression plate is displayed.

11. A mammography device as claimed in claim 10 wherein said superimposing device generates a visible image of said virtual mask on said compression plate, and allows displacement of said breast until the position and contour of the breast substantially coincide with a position and contour of said image of said mask.

12. A mammography device as claimed in claim 11 wherein said superimposing device generates said image of said mask on said compression plate as a projection image projected onto said compression plate.

13. A mammography device as claimed in claim 11 wherein said superimposing device generates, in said image, a displacement vector that indicates a direction and extent for displacement of the breast that are necessary to cause the position and contour of the breast to substantially coincide with the position and contour of the image of the virtual mask.

14. A mammography device as claimed in claim 10 wherein said superimposing device comprises a camera that generates a camera image of the breast in the mammography device and a portion of the compression plate containing said opening, and wherein said superimposing device superimposes said virtual mask on said camera image with said marked target region in said opening in said camera image, and allows displacement of the breast until a position and contour of the breast in the camera image substantially coincides with a position and contour of the mask superimposed on said camera image.

15. A mammography device as claimed in claim 14 wherein said camera, in said camera image, generates a displacement vector that indicates a direction and extent that are necessary to cause the position and contour of the breast in the camera image to substantially coincide with the position and contour of the virtual mask superimposed on the camera image.

* * * * *